United States Patent [19]
Vecchietti et al.

[11] Patent Number: 5,254,564
[45] Date of Patent: Oct. 19, 1993

[54] SUBSTITUTED ISOQUINOLINE COMPOUNDS, PHARMACEUTICAL COMPOSITION AND METHOD OF USE IN TREATING PAIN IN MAMMALS

[75] Inventors: Vittorio Vecchietti; Giuseppe Giardina; Roberto Colle, all of Milan, Italy

[73] Assignee: Lo Zambeletti S.p.A., Italy

[21] Appl. No.: 553,723

[22] Filed: Jul. 16, 1990

[30] Foreign Application Priority Data

Jul. 18, 1989 [GB] United Kingdom ............ 8916395

[51] Int. Cl.$^5$ .................. A61K 31/47; C07D 217/26
[52] U.S. Cl. ................................. 514/307; 544/363; 546/18; 546/79; 546/146; 546/147
[58] Field of Search .................. 546/146-147; 514/307

[56] References Cited

U.S. PATENT DOCUMENTS

| | | | |
|---|---|---|---|
| 3,985,881 | 10/1976 | Mehrhof et al. | 546/146 |
| 4,806,547 | 2/1989 | Giardina et al. | 546/146 |
| 4,954,509 | 9/1990 | Vecchietti et al. | 546/146 |

FOREIGN PATENT DOCUMENTS

| | | |
|---|---|---|
| 0232989 | 8/1987 | European Pat. Off. ......... 546/146 |
| 330360 | 8/1989 | European Pat. Off. |
| 0409489 | 1/1991 | European Pat. Off. ......... 546/146 |

Primary Examiner—C. Warren Ivy
Assistant Examiner—James H. Turnipseed
Attorney, Agent, or Firm—Rosenman & Colin

[57] ABSTRACT

A compound, or a solvate or salt thereof, of formula (I):

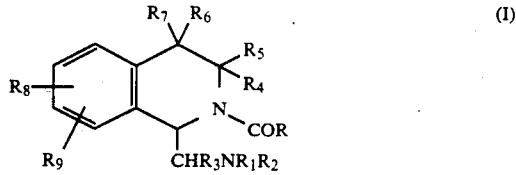

in which:

RCO is an acyl group in which the group R contains a substituted or unsubstituted carbocyclic aromatic or heterocyclic aromatic ring and $R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group optionally substituted with a hetero-atom;

$R_3$ is hydrogen, $C_{1-6}$ alkyl, preferably methyl or ethyl, $^4$or phenyl, or $R_3$ together with $R_1$ forms a —(CH$_2$)$_3$— or —(CH$_2$)$_4$—, group;

$R_4$ and $R_5$ are identical and are hydrogen or $C_{1-6}$ alkyl, or together form a $C_{2-5}$ linear polymethylene group; $R_6$ and $R_7$ are identical and are hydrogen or $C_{1-6}$ alkyl, or together form a $C_{2-5}$ linear polymethylene group;

or $R_5$ and $R_6$ are together —CH$_2$— when each of $R_4$ and $R_7$ is hydrogen or $C_{1-6}$ alkyl;

with the proviso that $R_4$, $R_5$, $R_6$ and $R_7$ are not simultaneously hydrogen;

$R_8$ and $R_9$, which may be the same or different, are each hydrogen, $C_{1-6}$ alkyl, —CH$_2$OR$_{10}$, halogen, hydroxy, $C_{1-6}$ alkoxy, $C_{1-6}$ alkoxycarbonyl, thiol, $C_{1-6}$ alkylthio,

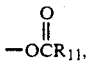

—NHCOR$_{12}$, —NHSO$_2$R$_{13}$, —CH$_2$SO$_2$NR$_{14}$R$_{15}$, in which each of R$_{10}$ to R$_{15}$ is independently hydrogen, $C_{1-6}$ alkyl, aryl or aralkyl, is useful for the treatment of pain, and or hyponatraemic disease states and/or cerebral ischaemia.

5 Claims, No Drawings

SUBSTITUTED ISOQUINOLINE COMPOUNDS, PHARMACEUTICAL COMPOSITION AND METHOD OF USE IN TREATING PAIN IN MAMMALS

This invention is concerned with novel isoquinoline derivatives, processes for their preparation, and their use in medicine, particularly as analgesics.

Compounds which are kappa-receptor agonists act as analgesics through interaction with kappa opioid receptors. The advantage of kappa-receptor agonists over the classical $\mu$-receptor agonists, such as morphine, lies in their ability to cause analgesia while being devoid of morphine-like behavioural effects and addiction liability.

European Published Application No. 330360 discloses a group of substituted isoquinoline derivatives which exhibit kappa-receptor agonism without some of the behavioural effects of morphine and morphine analogues, and which are thus of potential therapeutic utility as analgesics.

A novel class of structurally related substituted isoquinolines has now been discovered which also exhibit potent kappa-receptor agonism without the aforementioned undesirable behavioural effects. Compounds of the novel class also demonstrate long duration of action and reduced sedative potential.

In addition, the novel isoquinolines possess diuretic activity which indicates that they are of potential use in the treatment of hyponatraemic diseases states in mammals. They are also of potential use in the treatment of cerebral ischaemia.

According to the present invention there is provided a compound, or a solvate or salt thereof, of formula (I):

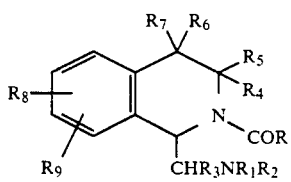

in which:
RCO is an acyl group in which the group R contains a substituted or unsubstituted carbocyclic aromatic or heterocyclic aromatic ring and $R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group optionally substituted with a hetero-atom;
$R_3$ is hydrogen, $C_{1-6}$ alkyl, preferably methyl or ethyl, or phenyl, or $R_3$ together with $R_1$ forms a $-(CH_2)_3-$ or $-(CH_2)_4-$, group;
$R_4$ and $R_5$ are identical and are hydrogen or $C_{1-6}$ alkyl, or together form a $C_{2-5}$ linear polymethylene group; $R_6$ and $R_7$ are identical and are hydrogen or $C_{1-6}$ alkyl, or together form a $C_{2-5}$ linear polymethylene group;
or $R_5$ and $R_6$ are together $-CH_2-$ when each of $R_4$ and $R_7$ is hydrogen or $C_{1-6}$ alkyl;
with the proviso that $R_4$, $R_5$, $R_6$ and $R_7$ are not simultaneously hydrogen;
$R_8$ and $R_9$, which may be the same or different, are each hydrogen, $C_{1-6}$ alkyl, $-CH_2OR_{10}$, halogen, hydroxy, $C_{1-6}$ alkoxy, $C_{1-6}$ alkoxycarbonyl, thiol, $C_{1-6}$ alkylthio,

$-NHCOR_{12}$, $-NHSO_2R_{13}$, $-CH_2SO_2NR_{14}R_{15}$, in which each of $R_{10}$ to $R_{15}$ is independently hydrogen, $C_{1-6}$ alkyl, aryl or aralkyl. Examples of aryl and aralkyl groups are phenyl and benzyl respectively.

Examples of substituents are:
$R_4$ and $R_5$ are both $C_{1-6}$ alkyl, preferably methyl, when each of $R_6$ and $R_7$ is hydrogen;
$R_6$ and $R_7$ are both $C_{1-6}$ alkyl, preferably methyl, when each of $R_4$ and $R_5$ is hydrogen;
$R_6$ and $R_7$ together form a $C_{2-5}$ linear polymethylene group, preferably $-(CH_2)_2-$, when each of $R_4$ and $R_5$ is hydrogen;
$R_5$ and $R_6$ are together $-CH_2-$ when each of $R_4$ and $R_7$ is hydrogen.

When used herein, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

When the carbocyclic or heterocyclic group is a fused two ring system, one or both rings may be aromatic in character.

Suitably, one of the rings is aromatic and the other is non-aromatic.

The $C_{1-6}$ alkyl groups may be either straight or branched chain and examples are methyl, ethyl, propyl, n-butyl, n-pentyl or n-hexyl, preferably methyl.

Examples of $C_{2-6}$ alkenyl groups are 1- and 2- propenyl; an example of a $C_{3-6}$ cycloalkyl group is cyclopropyl, and an example of a $C_{4-12}$ cycloalkylalkyl group is cyclopropylmethyl.

When $R_1$ and $R_2$ together form a linear or branched polymethylene group, examples are propylene, butylene, pentylene or hexylene, preferably butylene or 1-methylbutylene. As an alkenylene group, $R_1$-$R_2$ may be typically $-CH_2-CH=CH-CH_2-$. Examples of hetero-atoms are oxygen and sulphur, particularly oxygen, and a suitable hetero-atom substituted polymethylene group is $-CH_2CH_2OCH_2CH_2-$.

The group R preferably has the formula (II):

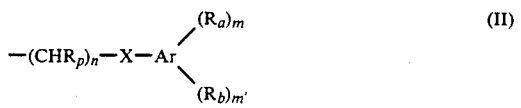

in which
n is 0, 1 or 2;
m is 0, 1 or 2;
m' is 0, 1 or 2, provided $m+m' \leq 3$
X is a direct bond, or O, S or $NR_c$ in which $R_c$ is hydrogen or $C_{1-6}$ alkyl;
Ar is a substituted or unsubstituted carbocyclic or heterocyclic aromatic group;
each of $R_a$ and $R_b$ is $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, phenyl, phenyl $C_{1-6}$ alkyl, hydroxy, $C_{1-6}$ alkoxy, thiol, $C_{1-6}$ alkylthio, $C_{1-6}$ haloalkoxy, $C_{1-6}$ haloalkylthio, halogen, $NO_2$, CN, $CF_3$, —OCF$_3$, —OCHF$_2$, —OCF$_2$CF$_2$H, —OCCl$_2$CF$_3$, —COOR$_d$, —CONR$_e$R$_f$, —SO$_3$Rg, —SO$_2$NR$_h$R$_k$ and —COR$_m$ in which each of R$_d$ to R$_m$ is independently hydrogen, C$_{1-6}$ alkyl, phenyl or phenyl C$_{1-6}$ alkyl;

or, when m is 2 and m' is O, two R$_a$'s form a C$_{2-6}$ polymethylene group;

and R$_p$ is hydrogen or C$_{1-6}$ alkyl, such as methyl or ethyl.

Preferred halogens are F, Cl and Br.

When Ar is a carbocyclic aromatic group, it is preferably phenyl, and R$_a$ or R$_b$ is preferably in the meta and/or para position.

Other examples of Ar are thienyl, naphthyl, benzothienyl, benzofuranyl, 2,3-dihydrobenzofuranyl, 2,3-dihydrobenzothienyl, indolyl, 2,3-dihydrobenzopiranyl and 2,3-dihydrobenzothiopiranyl.

Preferably R$_a$ or R$_b$ is bromine, chlorine, NO$_2$ or CF$_3$, particularly in the meta- or para- position.

X is typically oxygen or a direct bond, and n is typically 1.

Particular examples of the group R are:

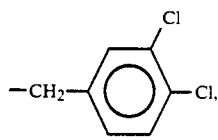

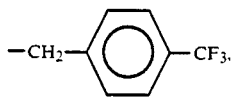

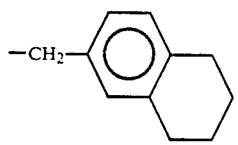

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula (III):

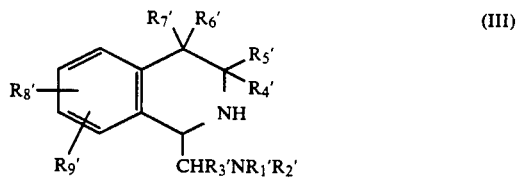

in which R$_1'$, R$_2'$, R$_3'$, R$_4'$, R$_5'$, R$_6'$, R$_7'$, R$_8'$ and R$_9'$ are R$_1$ to R$_9$ respectively as defined for formula I, or each is a group or atom convertible to R$_1$ to R$_9$ respectively.

with a compound of formula R'CO.OH or an active derivative thereof, in which R' is as defined for formula (I), or a group convertible to R, to form a compound of formula (Ia)

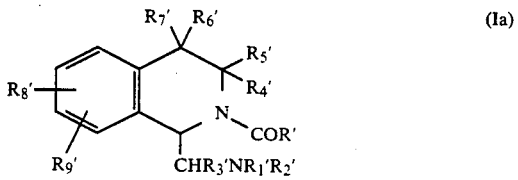

and then optionally performing one of the following steps:

a) where R', R$_1'$, R$_2'$ R$_3'$, R$_4'$, R$_5'$, R$_6'$, R$_7'$, R$_8'$ and R$_9'$ are other than R, R$_1$, R$_2$, R$_3$, R$_4$, R$_5$, R$_6$, R$_7$, R$_8$ and R$_9$ converting R', R$_1'$, R$_2'$ R$_3'$, R$_4'$, R$_5'$, R$_6'$, R$_6'$ R$_8'$ and R$_9'$ to R, R$_1$, R$_2$, R$_3$, R$_4$, R$_5$, R$_6$, R$_7$, R$_8$ and R$_9$ to obtain a compound of formula (I), b) where R', R$_1'$, R$_2'$ R$_3'$, R$_4'$, R$_5'$, R$_6'$, R$_7'$, R$_8'$ and R$_9'$ are R, R$_1$, R$_2$, R$_3$, R$_4$, R$_5$, R$_6$, R$_7$, R$_8$ and R$_9$ converting one R, R$_1$, R$_2$, R$_3$, R$_4$, R$_5$, R$_6$, R$_7$, R$_8$ and R$_9$ to another R, R$_1$, R$_2$, R$_3$, R$_4$, R$_5$, R$_6$, R$_7$, R$_8$ and R$_9$ to obtain a compound of formula (I), c) forming a salt and/or solvate of the obtained compound of formula (I).

Suitable active derivatives of R'CO.OH are acid chlorides or acid anhydrides. Another suitable derivative is a mixed anhydride formed between the acid and an alkyl chloroformate.

For example, in standard methods well known to those skilled in the art, the compound of formula III may be coupled:

a) with an acid chloride in the presence of an inorganic or organic base, b) with the acid in the presence of dicyclohexyl carbodiimide, N-dimethylaminopropyl-N'-ethyl carbodiimide or carbonyl diimidazole, c) with a mixed anhydride generated in situ from the acid and an alkyl (for example ethyl) chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

For example, R$_1'$ and R$_2'$ may be alkyl groups and converted to R$_1$ or R$_2$ hydrogen atoms by conventional substituted benzyl it may be converted to an $R_1$ or $R_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process can provide a diastereoisomeric mixture which can be subsequently separated into isomers by column chromatography.

The compound R'CO.OH is typically of the formula (IIa):

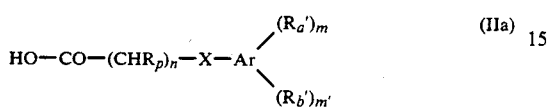

in which $R_a'$ and $R_b'$ are $R_a$ and $R_b$ as defined for formula (II), or a group or atom convertible to $R_a$ or $R_b$, the other variables being as defined for formula (II).

Conversions of substituents $R_a'$ or $R_b'$ on the aromatic group Ar to obtain $R_a$ or $R_b$ are generally known in the art of aromatic chemistry. $R_a'$ is preferably $R_a$ and $R_b'$ is preferably $R_b$.

A preferred reagent is the equivalent acid halide of formula (IIb):

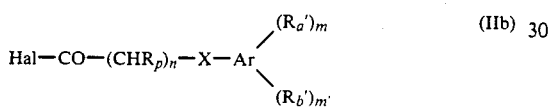

in which Hal is a halogen, typically chlorine or bromine.

The compounds of formula (I) may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I and their intermediates exist in more than one stereoisomeric form and the processes of the invention produces mixtures thereof. The individual enantiomers may be obtained by resolution of the compounds of formula (I) using an optically active acid such as tartaric acid or by resolution of the intermediate diamines of formula (III) using an optically active acid chloride such as S(-) camphanic chloride.

Alternatively, an asymmetric synthesis would offer a route to individual enantiomers.

The compounds of formula (III) may be obtained from a 3,4-dihydroisoquinoline compound of formula (IV) in which $R_3'$, $R_4'$, $R_5'$, $R_6'$, $R_7'$, $R_8'$ and $R_9'$ have the meanings defined for formula (III), by treatment with an amine of formula $NHR_1'R_2'$ (where $R_1'$ and $R_2'$ are as defined above) followed by reaction of the formed compound of formula (V) with $NaBH_4$ or with hydrogen in the presence of a 5% palladium on charcoal catalyst, in accordance with the following reaction scheme:

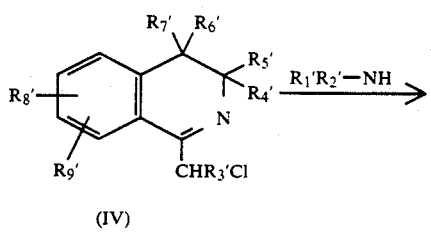

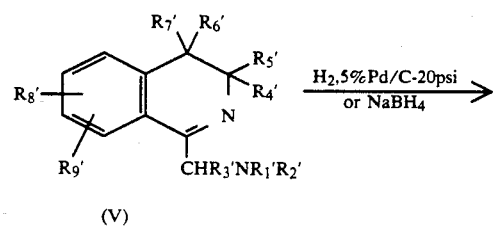

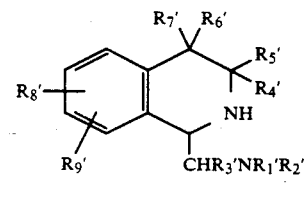

The compounds of formula (IV) may themselves by prepared by treating a compound of formula (VI)

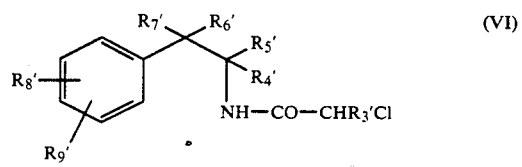

in which $R_3'$, $R_4'$, $R_5'$, $R_6'$, $R_7'$, $R_8'$ and $R_9'$ are as defined in formula (III) with phosphorus pentoxide in the presence of an organic solvent such as xylene.

The compounds of formula (VI) are known compounds or can be prepared from known compounds by known methods [see, for example, DE-A-1,934,918; C.A.. Vol. 72 (1970) 100322m; Acta. Pharm. Svecica 1970, 7(5), 543–50; C.A. Vol. 74 (1971) 64032x].

The compounds of formula (III) can be separated into their pure enantiomers by first protecting the NH group with an alkyl or benzyl chloroformate, resolving the compound thus formed using an active acid, such as O,O'-di-p-toluoyl tartaric acid, and subsequently deprotecting the optically active alkyl or benzyl carbamates in accordance with standard methods.

Alternatively, compounds of formula (III) may be treated with an optically active acid chloride, such as S(—)- camphanic chloride, and the pure enantiomers can be obtained by hydrolysis of the separated diastereomeric amides.

The intermediate compounds of formula (III) above are novel compounds and, as such, they form a further aspect of this invention.

The activity of the compounds of formula (I) in standard tests indicates that they are of potential therapeutic utility in the treatment of pain, hyponatraemic disease states, and cerebral ischaemia.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, or in the manufacture of a medicament for the treatment of hyponatraemic diseases states, or in the manufacture of a medicament for the treatment of cerebral ischaemia.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents or diuretics or agents for treating cerebral ischaemia.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or as a diuretic, or for the treatment of cerebral ischaemia.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling or tabletting. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, for example sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method for the treatment and/or prophylaxis of pain and/or hyponatraemic disease states and/or cerebral ischaemia in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples, while the Descriptions illustrate the preparation of intermediates.

The compounds of the Descriptions are summarised in Tables I and II, and the compounds of the Examples in Table III.

DESCRIPTION 1

1-chloromethyl-4,4-dimethyl-3,4-dihydroisoquinoline hydrochloride 11.0 g (48.73 mmoles) of N-(2-phenyl-2-methyl)propyl-2-chloroacetamide [DE-A-1, 934,918-22.1.1970(C.A. 72-100322m); Acta Pharm. Svecica 1970, 7(5), 543-50 (C.A. 74-64032x)] were added portionwise under nitrogen to a slurry of 43 g of phosphorus pentoxide in 200 ml of xylene at 140° C.

The reaction mixture was refluxed and vigourously stirred for 3 hours; the xylene was decanted off and the solid residue carefully treated with 700 ml of cold water in an ice bath. The resulting solution was extracted with diethyl ether, brought to basic pH with HCl/diethyl ether and concentrated in vacuo to dryness.

The crude solid was triturated in 70 ml of ethyl acetate, filtered, washed and dried, to yield 10.1 g (84%) of the title compound.

$C_{12}H_{14}ClN \cdot HCl$
M.P. = 176°-178° C.
M.W. = 244.162

Analogously, the following compounds shown in Table I were prepared.

DESCRIPTION 2

1-(pyrrolidin-1-yl)methyl-4,4-dimethyl-1,2,3,4-tetrahydroisoquinoline 3.0 g (12.29 mmoles) of 1-chloromethyl-4,4-dimethyl-3,4-dihydroisoquinoline hydrochloride were added portionwise under nitrogen atmosphere to a stirred solution of 5 ml of pyrrolidine in 60 ml of methanol, cooled below −5° C. The stirring was continued 24 hours at room temperature and the nitrogen atmosphere maintained all the time. The solution was then cooled to 0° C., and 1.0 g (125 mmoles) of sodium borohydride added.

After three hours 2 ml of conc. NaOH solution were added and
inorganic salts filtered off.

The filtrate was concentrated in vacuo to afford a residue which was treated with Conc. NaOH solution and exhaustively extracted with diethyl ether.

The ethereal solution was filtered over celite, dried over $Na_2SO_4$ and the solvent evaporated in vacuo to dryness, to yield 3.0 g of the title compound.

$C_{16}H_{24}N_2$
B.P. (0.2mmHg) = 115°-120° C.
M.W. = 244.368

Analogously, the following compounds shown in Table II were prepared.

TABLE I

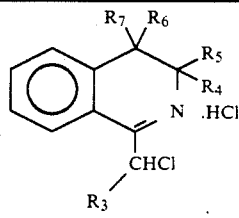

| R3 | R4 | R5 | R6 | R7 | MOLECULAR FORMULA | MELTING POINT °C. | YIELD | N.M.R.(CDCl3) 80MHz |
|---|---|---|---|---|---|---|---|---|
| H | H | H | CH3 | CH3 | C12H14ClN.HCl | 176-178 | 84% | δ7.3-8.1(m, 4H); 5.3(s, 2H); 3.8 (s, 2H); 1.4(s, 6H). |
| H | CH3 | CH3 | H | H | C12H14ClN.HCl | 167-170 | 21% | δ7.3-8.2(m, 4H); 5.4(s, 2H); 3.1 (s, 2H); 1.6(s. 6H). |
| H | H | —CH2— | | H | C11H10ClN.HCl | 170-173 | 51%* | δ7.4-8.2(m, 4H); 5.2(AB system, J=12.1 Hz. 2H); 3.9-4.1(m, 1H); 2.8-3.1(m, 1H); 2.1-2.5(m, 1H); 0-0.3(m, 1H). |
| H | H | H | —CH2—CH2— | | C12H12ClN.HCl | oil | 23%** | |

*1,1,2,2-tetrachloroethane was used as reaction solvent.
**The reaction was carried out in toluene by heating 2 h at 70° C.

TABLE II

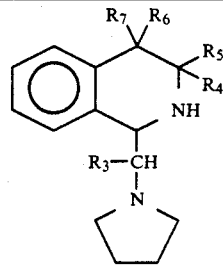

| R3 | R4 | R5 | R6 | R7 | MOLECULAR FORMULA | YIELD | b.p. °C./mmHg |
|---|---|---|---|---|---|---|---|
| H | H | H | CH3 | CH3 | C16H24N2 | >95% | 115-120/0.2 |
| H | CH3 | CH3 | H | H | C16H24N2 | >95% | * |
| H | H | —CH2— | | H | C15H20N2 | >95% | * |

TABLE II-continued

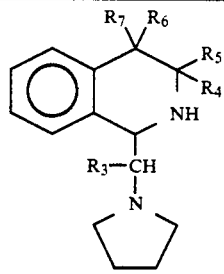

| R3 | R4 | R5 | R6 | R7 | MOLECULAR FORMULA | YIELD | b.p. °C./mmHg |
|----|----|----|----|----|------------------|-------|---------------|
|    |    |    |    |    | (Diastereoisomeric mixture) |  |  |
| H  | H  | H  | —CH$_2$—CH$_2$— | | C$_{16}$H$_{22}$N$_2$ | >80% | * |

*Used for the subsequent reaction without further purification.

EXAMPLE 1

1-(pyrrolidin-1-yl)methyl-2-(3,4-dichlorophenyl)acetyl-4,4-dimethyl-1,2,3,4-tetrahydroisoquinoline hydrochloride 2.98 g (12.19 mmoles) of 1-(pyrrolidin-1-yl)methyl-4,4-dimethyl-1,2,3,4-tetrahydroisoquinoline were dissolved in 60 ml of dry chloroform.

3.6 g (26.08 mmoles) of anhydrous potassium carbonate were added and the solution cooled at −5° C.

3.2 g (14.31 mmoles) of 3,4-dichlorophenylacetyl chloride, dissolved in 10 ml of chloroform, were added dropwise and the solution was allowed to reach room temperature and left overnight.

20 ml of water were added and the biphasic solution stirred for 30'; the organic layer was separated, washed with 5% NaOH solution, then with H$_2$O and dried over Na$_2$SO$_4$.

The solvent was evaporated in vacuo to dryness and the residue was dissolved in 70 ml of ethyl acetate. The solution was brought to acidic pH with HCl/diethyl ether and the precipitate was filtered, washed and dried to yield 4.2 g of the title compound.

C$_{24}$H$_{28}$Cl$_2$N$_2$O . HCl
M.P.=270°–273° C.
M.W.=467.859
Elemental analysis: Calcd. C,61.61; H,6.25; N,5.99; Cl,22.74;
Found C,61.44; H,6.26; N,5.95; Cl,22.46.
I.R. (KBr): 1625 (s); 1440 (s) cm$^{-1}$.

| M.M.R.(CDCl$_3$) 80Mhz | δ11.80(s broad, 1H); 6.90-7.50(m, 7H); 6.10(dd, 1H); 4.02(AB system, J=16.2Hz, 2H); 3.40-4.30(m, 5H); 2.50-3.30(m, 3H); 1.80-2.40(m, 4H); 1.40(s, 3H); 1.20 (s, 3H). |
|---|---|

EXAMPLE 2

1-(pyrrolidin-1-yl)methyl-2-(4-trifluoromethylphenyl)acetyl-4,4-dimethyl-1,2,3,4-tetrahydroisoquinoline Prepared as Ex. No. 1, from 2.44 g (10.0 mmoles) of 1-(pyrrolidin-1-yl)methyl-4,4-dimethyl-1,2,3,4-tetrahydroisoquinoline, 3.04 g (22.0 mmoles) of anhydrous potassium carbonate and 2.45 g (11.01 mmoles) of 4-trifluoromethylphenylacetyl chloride in 40 ml of dry chloroform.

The work up of the reaction mixture was carried out in the same manner described in Ex. No. 1.

The crude free base was crystallized from 100 ml of hexane to yield 2.4 g of the title compound.

C$_{25}$H$_{29}$F$_3$N$_2$O
M.P.=108°–109° C.
M.W.=430.498
Elemental analysis: Calcd. C,69.75; H,6.79; N,6.51; F,13.24;
Found C,69.86; H,6.81; N,6.47; F,13.22.

EXAMPLE 3

1-(pyrrolidin-1-yl)methyl-2-(5,6,7,8-tetrahydronapht-2-yl) acetyl-4,4-dimethyl-1,2,3,4-tetrahydroisoquinoline hydrochloride 1.10 g (4.51 mmoles) of 1-(pyrrolidin-1-yl)methyl-4,4-dimethyl-1,2,3,4-tetrahydroisoquinoline and 1.03 g (5.42 mmoles) of 5,6,7,8-tetrahydronapht-2-yl acetic acid were dissolved in 40 ml of dry chloroform.

2.0 g (9.75 mmoles) of dicyclohexylcarbodiimide, dissolved in 10 ml of chloroform, were added dropwise to this solution, at −5° C. The reaction mixture was allowed to reach room temperature, stirred 6 hours and left overnight.

The precipitated dicyclohexylurea was filtered off and the solution was evaporated in vacuo to dryness.

The residual oil was flash chromatographed on 230-400 mesh silica gel, eluting with hexane/ethyl acetate 1:1 containing 0.25% NH$_4$OH, to afford 1 g of the free base which was dissolved in 50 ml of ethyl acetate and the solution brought to acidic pH with HCl/diethyl ether. The precipitate was filtered, washed and dried, to yield 900 mg of the title compound.

C$_{28}$H$_{36}$N$_2$O . NCl
M.P.=215°–217° C.
M.W.=453.049
Elemental analysis: Calcd. C,74.23; H,8.23; N,6.18; Cl,7.83;
Found C,74.24; H,8.25; N,6.14; Cl,7.76.
I.R. (KBr): 1630 (s); 1440 (m) cm$^{-1}$.

| N.M.R.(CDCl$_3$) 80Mhz | δ11.80(s, broad, 1H); 6.85-7.40(m, 7H); 6.15(dd, 1H); 3.98(AB system, J=16.2 Hz, 2H); 3.88(s, 2H); 3.40-4.30(m, 3H); 2.45-3.15(m, 7H); 1.90-2.40(m, 4H); 1.55-1.85(m, 4H); 1.35(s, 3H); 1.20 (s, 3H). |
|---|---|

EXAMPLE 4

1-(pyrrolidin-1-yl)methyl-2-(3,4-dichlorophenyl)acetyl-3,3-dimethyl-1,2,3,4-tetrahydroisoquinoline hydrochloride Prepared as Ex. No. 1, from 2.47 g (10.11 mmoles) of 1-(pyrrolidin-1-yl)methyl-3,3-dimethyl-1,2,3,4-tetrahydroisoquinoline, 3.07 g ( 22.24 mmoles) of anhydrous potassium carbonate and 2.48 g 11.10 mmoles) of 3,4-dichlorophenyl acetyl chloride in 50 ml to dry chloroform.

The work up of the reaction mixture was carried out in the same manner described in Ex. No. 1.

The residue was dissolved in 70 ml of acetone and the solution was brought to acidic pH with HCl/diethyl ether. The precipitate was filtered, washed and dried, to yield 2.1 g of the title compound.

$C_{24}H_{28}Cl_2N_2O \cdot HCl$
M.P.=219°-221° C.
M.W.=467.859
Elemental analysis: Calcd. C,61.61; H,6.25; N,5.99; Cl,22.74;
Found C,61.35; H,6.25; N,5.98; Cl,22.59,
I.R. (KBr) : 1630 (s); 1435 (s) cm$^{-1}$.
N.M.R. (CDCl ) : $\delta$12.90 (s, broad, 1H); 7.00-7.70 (m,7H); 5.95 (dd, 1H); 3.60-4.20 (m, 3H); 2.40-3.30 (m, 7H); 1.50-2.10 (m, 4H); 1.70 (s, 3H); 1.10 (s, 3H).

EXAMPLE 5

2-(3,4-dichlorophenyl)acetyl-3-(pyrrolidin-1-yl)methyl-1a,2,3,7b-tetrahydro-1H-cycloprop[c]isoquinoline hydrochloride Diastereoisomer TRANS Prepared as Ex. No. 1, from 4.0 g (17.52 mmoles) of 3-(pyrrolidin-1-yl)methyl-1a,2,3,7b-tetrahydro-1H-cyloprop[c] isoquinoline (mixture of diastereoisomeric diamines), 4.83 g (35.00 mmoles) of anhydrous potassium carbonate and 4.07 g (18.21 mmoles) of 3,4-dichlorophenylacetyl chloride in 90 ml of dry chloroform.

The work up of the reaction mixture was carried out in the same manner described in Ex. No. 1.

The residue was flash chromatographed over 230-400 mesh ASTM silica gel, eluting with ethyl acetate containing 1% of NH$_4$OH, to afford 180 mg of the least polar product which was dissolved in 15 ml of ethyl acetate and the solution brought to acidic pH with HCl/diethyl ether.

The precipitate was filtered, washed and dried, to yield 130 mg of the title compound.

$C_{23}H_{24}Cl_2N_2O \cdot HCl$
M.P.=173°-177° C.
M.W.=451.817
I.R. (KBr) : 1630 (s) cm$^{-1}$.

| N.M.R.(CDCl$_3$): 80Mhz | $\delta$11.70(s, broad, 1H); 7.00-7.50(m, 7H); 6.10(d, broad, 1H); 1.80-4.50(m, 14H); 1.20-1.60(m, 1H); 0.80-1.15(m, 1H). |
|---|---|

EXAMPLE 6

2-(3,4-dichlorophenyl)acetyl-3-(pyrrolidin-1-yl)methyl-1a,2,3,7b-tetrahydro-1H-cycloprop[c]isoquinoline Diastereoisomer CIS Continuing the elution of the chromatographic column described in Ex. No. 5, a second product was obtained and crystallized as free base from n-hexane to yield 6.6 g of the title compound.

$C_{23}H_{24}Cl_2N_2O$
M.P.=119°-120° C.
M.W.=415.352
Elemental analysis: Calcd. C,66.51; H,5.82; N,6.75; Cl,17.07;
Found C,66.82; H,5.83; N,6.74; Cl,17.05.
I.R. (KBr) : 1645 (s); 1415 (s); 760 (m) cm$^{-1}$.

| N.M.R.(CDCl$_3$): 80Mhz | $\delta$7.10-7.50(m, 7H); 5.45(dd, 1H); 3.90(AB system, J=15.5Hz, 2H); 2.15-3.15(m, 8H); 1.55-1.85(m, 4H); 1.25-1.55(m, 1H); 0.55-0.80(m, 1H). |
|---|---|

EXAMPLE 7

1-(pyrrolidin-1-yl)methyl-2-(3,4-dichlorophenyl)acetyl spiro [1,2-dihydroisoquinoline-4(3H),1'-cyclopropane]hydrochloride hemihydrate Prepared as Ex. No. 1, from 2.70 g (11.15 mmoles) of crude 1-(pyrrolidin-1-yl)methyl spiro [1,2-dihydroisoquinoline-4(3H),1'-cyclopropane], 3.08 g (22.32 mmoles) of anhydrous potassium carbonate and 2.74 g (12.25 mmoles) of 3,4-dichlorophenylacetyl chloride in 50 ml of dry chloroform. The work up of the reaction mixture was carried out in the same manner described in Ex. No. 1.

The residue was flash chromatographed over 230-400 mesh ASTM silica gel, eluting with a mixture of ethyl acetate/hexane/32% NH$_4$OH, 35:15:0.4 respectively, to afford 1.2 g of the free base, which was dissolved in 60 ml of ethyl acetate and the solution brought to acidic pH with HCl/diethyl ether.

The precipitate was filtered and recrystallized from 25ml of cold methanol to yield 900 mg of the title compound.

$C_{24}H_{26}Cl_2N_2O \cdot HCl \cdot \frac{1}{2}H_2O$
M.P.=230°-232° C.
M.W.=474.851
Elemental analysis: Calcd. C,60.70; H,5.94; N,5.90; Cl,22.40;
Found C,60.58; H,5.89; N,5.86; Cl,22.41.
I.R. (KBr): 1635 (s) 1440 (s) cm$^{-1}$.

| N.M.R.(CDCl$_3$): 80Mhz | $\delta$11.80(s, broad, 1H); 6.95-7.50(m, 6H); 6.70-6.90(m, 1H); 6.12(dd, 1H); 3.30-4.45(m, 7H); 2.45-3.25(m, 3H); 1.80-2.40(m, 4H); 0.75-1.30(m, 4H). |
|---|---|

DESCRIPTION 3

1-(pyrrolidin-1-yl)methyl-2-camphanoyl-4,4-dimethyl-1,2,3,4-tetrahydroisoquinoline. Diastereoisomer A Prepared as Ex. No. 1, from 6.20 g (25.37 mmoles) of the compound of Description 2, 6.40 g (46.37 mmoles) of anhydrous potassium carbonate and 5.00 g (23.07 mmoles) of (S)-(−)-camphanic acid chloride in 100 ml of dry chloroform. The work up of the reaction mixture was carried out in the same manner described in Ex. No. 1.

The residue was flash chromatographed over 230-400 mesh ASTM silica gel, eluting with a mixture of hexane/ethyl acetate/25% NH$_4$OH, 40:10:0.15 respectively, to yield 4.3 g of the title compound which was the least polar product.

$C_{26}H_{36}N_2O_3$

M.W.=424.564

I.R. (neat): 1790 (s); 1620 (s); 1445 (s); 1100 (s) cm$^{-1}$.

$[\alpha]_D^{20}$=+3.4 (C=1, CHCl$_3$).

DESCRIPTION 4

1-(pyrrolidin-1-yl)methyl-2-camphanoyl-4,4-dimethyl-1,2,3,4-tetrahydroisoquinoline. Diastereoisomer B Continuing the elution of the flash chromatographic column of the description n° 3, 4.8 g of the title compound were obtained as the second product.

$C_{26}H_{36}N_2O_3$

M.W.=424.564

I.R. (neat): 1790 (s); 1645 (s); 1440 (s); 1100 (s) cm$^{-1}$.

$[\alpha]_D^{20}$=−65.4 (C=1, CHCl$_3$).

DESCRIPTION 5

(−)-1-(pyrrolidin-1-yl)methyl-4,4-dimethyl-1,2,3,4-tetrahydroisoquinoline 4.3 g of the compound of description No. 3 (Diast. A) were dissolved in 150 ml of acetic acid and treated with 100 ml of 48% HBr, 7 days at 130° C.

The solvent was evaporated in vacuo to dryness and the residue dissolved in 60 ml of water. The acidic solution was extracted twice with diethyl ether and then carefully treated with conc. NH$_4$OH solution at 0° C.

The basic solution was exhaustively extracted with diethyl ether, which was dried over Na$_2$SO$_4$ and the solvent evaporated in vacuo to dryness to afford 1.7 g of the crude product. The silica gel flash chromatography, eluting with a mixture of CH$_2$Cl$_2$/MeOH/32% NH$_4$OH, 94:5:0.5 respectively, afforded 700 mg of the title compound.

$C_{16}H_{24}N_2$

M.W.=244.368

$[\alpha]_D^{20}$=−36.6 (C=1, CHCl$_3$).

DESCRIPTION 6

(+)-1-(pyrrolidin-1-yl)methyl-4,4-dimethyl-1,2,3,4-tetrahydroisoquinoline 4.8 g of the compound of description No. 4 (Diast. B) were treated in the same reaction conditions of description No. 5. The silica gel flash chromatography afforded 1.42 g of the title compound.

$C_{16}H_{24}N_2$

M.W.=244.368

$[\alpha]_D^{20}$+37.2 (C=1, CHCl$_3$).

EXAMPLE 8

(+)-1-(pyrrolidin-1-yl)methyl-2-(3,4-dichlorophenyl)acetyl-4,4-dimethyl-1,2,3,4-tetrahydroisoquinoline hydrochloride Prepared as Ex. No. 1, from 700 mg (2.86 mmoles) of (−)-1-(pyrrolidin-1-yl)methyl-4,4-dimethyl-1,2,3,4-tetrahydroisoquinoline, 790 mg (5.72 mmoles) of anhydrous potassium carbonate and 740 mg (3.31 mmoles) of 3,4-dichlorophenylacetyl chloride in 40 ml of dry chloroform.

The work up of the reaction mixture was carried out in the same manner described in Ex. No. 1.

The crude product was dissolved in 30 ml of ethyl acetate and the solution brought to acidic pH with HCl/diethyl ether.

The precipitate was filtered, washed and dried, to yield 650 mg of the title compound.

$C_{24}H_{28}Cl_2N_2O \cdot HCl$

M.P.=248°-249° C.

M.W.=467.859

$[\alpha]_D^{20}$=+14.00 (C=1, MeOH).

I.R. and N.M.R. spectra were identical to those obtained for the racemate.

EXAMPLE 9

(−)-1-(pyrrolidin-1-yl)methyl-2-(3,4-dichlorophenyl)acetyl-4,4-dimethyl-1,2,3,4-tetrahydroisoquinoline hydrochloride Prepared as Ex. No. 1, from 1.42 g (5.81 mmoles) of (+)-1-(pyrrolidin-1-yl)methyl-4,4-dimethyl-1,2,3,4-tetrahydroisoquinoline, 1.60 g 911.59 mmoles) of anhydrous potassium carbonate and 1.50 g (6.71 mmoles) of 3,4-dichlorophenylacetyl chloride in 60 ml of dry chloroform.

The work up of the reaction mixture was carried out in the same manner described in Ex. No. 1.

The crude product was dissolved in 60 ml of ethyl acetate and the solution brought to acidic pH with HCl/diethyl ether.

The precipitate was filtered, washed and dried, to yield 1.3 g of the title compound.

$C_{24}H_{28}Cl_2N_2O \cdot HCl$

M.P.=248°-249° C.

M.W.=467.859

$[\alpha]_D^{20}$=−13.95 (C=1, MeOH).

I.R. and N.M.R. spectra were identical to those obtained for the racemate.

The Examples are summarised in Table III.

TABLE III

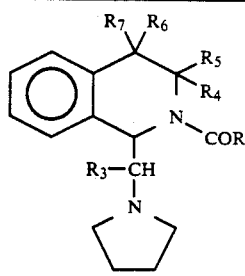

| Example No. | R | R3 | R4 | R5 | R6 | R7 | MOLECULAR FORMULA | MELTING POINT °C. | $[\alpha]_D^{20}$ (C = 1, MeOH) |
|---|---|---|---|---|---|---|---|---|---|
| 1 | $CH_2$—C6H3(Cl)(Cl) (3,4-diCl) | H | H | H | $CH_3$ | $CH_3$ | $C_{24}H_{28}Cl_2N_2O·HCl$ | 270–273 | — |
| 2 | $CH_2$—C6H4—$CF_3$ | H | H | H | $CH_3$ | $CH_3$ | $C_{25}H_{29}F_3N_2O$ | 108–109 | — |
| 3 | $CH_2$—(tetrahydronaphthyl) | H | H | H | $CH_3$ | $CH_3$ | $C_{28}H_{36}N_2O·HCl$ | 215–217 | — |
| 4 | $CH_2$—C6H3(Cl)(Cl) | H | $CH_3$ | $CH_3$ | H | H | $C_{24}H_{28}Cl_2N_2O·HCl$ | 219–221 | — |
| 5 DIAST. TRANS | $CH_2$—C6H3(Cl)(Cl) | H | H | —$CH_2$— | | H | $C_{23}H_{24}Cl_2N_2O·HCl$ | 173–177 | — |
| 6 DIAST. CIS | $CH_2$—C6H3(Cl)(Cl) | H | H | —$CH_2$— | | H | $C_{23}H_{24}Cl_2N_2O$ | 119–120 | — |
| 7 | $CH_2$—C6H3(Cl)(Cl) | H | H | H | —$CH_2$—$CH_2$— | | $C_{24}H_{26}Cl_2N_2O$ ·HCl·½ $H_2O$ | 230–232 | — |
| 8 | $CH_2$—C6H3(Cl)(Cl) | H | H | H | $CH_3$ | $CH_3$ | $C_{24}H_{28}Cl_2N_2O·HCl$ | 248–249 | +14.00 |

TABLE III-continued

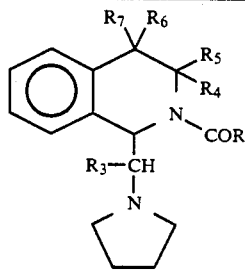

| Example No. | R | R3 | R4 | R5 | R6 | R7 | MOLECULAR FORMULA | MELTING POINT °C. | $[\alpha]_D^{20}$ (C = 1, MeOH) |
|---|---|---|---|---|---|---|---|---|---|
| 9 | CH₂-(2,3-dichlorophenyl) | H | H | H | CH₃ | CH₃ | $C_{24}H_{28}Cl_2N_2O \cdot HCl$ | 248-249 | −13.95 |

The pharmacological activity of the compounds of this invention is illustrated by various in vitro and in vivo models, using the following test procedures, in which the mousetail flick test demonstrates analgesic activity. The results are summarised in Table (IV).

PHARMACOLOGICAL TESTS

A) P-phenylquinone-induced abdominal writhing test in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25-36g body weight, were used. Animals were allowed food and water ad libitum and were randomized into groups of 10 prior to experimentation. Test compounds were dissolved in either distilled water or distilled water plus 0.1 M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perplex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

$$[1-(T/C)] \times 100\% = \% \text{ graded protection}$$

B) Tail-flick test in mice

The methodology employed is based on that described by D'Amour and Smith, J.Pharmacol. Exp. Ther. 72, 74/1941.

Male Charles River mice (Swiss Strain), 22≧34g body weight were used. Animals were allowed food and water ad libitum and were randomized into groups of 10 prior to experimentation. Before administration of the test compound, the reaction time of each animal was determined by focusing a beam of light onto the tail, eliciting a reflex withdrawal after a certain latency; only mice exhibiting a latency between 3-8 sec. were used subsequently in the evaluation of drug effects.

Test compounds were dissolved in either distilled water or distilled water plus 0.1 M AMS and administered by the subcutaneous route in a final volume of 10 ml/Kg. Control animals received 10 ml/Kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group.

TABLE IV

| Example No. | Mouse Writhing $ED^{50}$ mg/kg SUBCUTANEOUS* | Mouse Tail-Flick $ED^{50}$ mg/kg |
|---|---|---|
| 1 | 0.089 | 0.707 |
| 2 | 0.091 | 1.544 |
| 5 | 0.214 | 1.000 |
| 7 | ca 1 | 3.107 |
| 9 | 0.044 | 0.330 |

*Calculated for the free base

We claim:

1. A compound, or a solvate or salt thereof, of formula (I):

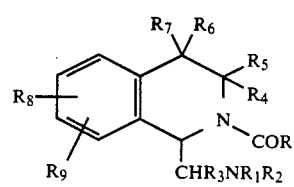

in which:

RCO is an acyl group in which the group R has the formula (II):

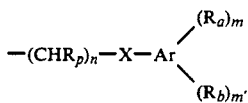

in which
n is 0, 1 or 2;
m is 0, 1 or 2;
m' is 0, 1 or 2, provided m+m' <3
x is a direct bond, or O, S or $NR_c$ in which $R_c$ is hydrogen or $C_{1-6}$ alkyl;
Ar is phenyl;
each of $R_a$ and $R_b$ is halogen;
or, when m is 2 and m' is O, two $R_a$'s form a $C_{2-6}$-polymethylene group;
and $R_p$ is hydrogen or $C_{1-6}$alkyl;
and $R_1$ and $R_2$ together form a pyrrolidin group; with the proviso that none of the remaining groups can combine to form a fused or spiro ring with the isoquinoline ring system;
$R_3$ is hydrogen, $C_{1-6}$ alkyl, or phenyl;
$R_4$ and $R_5$ are identical and are hydrogen or $C_{1-6}$ alkyl;
$R_6$ and $R_7$ are identical and are hydrogen or $C_{1-6}$ alkyl; with the provision that $R_4$, $R_5$, $R_6$ and $R_7$ are not simultaneously hydrogen;
$R_8$ and $R_9$, which may be the same or different, are each hydrogen, $C_{1-6}$ alkyl, $-CH_2OR_{10}$, halogen, hydroxy, $C_{1-6}$alkoxy, $C_{1-6}$alkoxycarbonyl, thiol, $C_{1-6}$alkylthio,

$-NHCOR_{12}$, $-NHSO_2R_{13}$, $-CH_2SO_2NR_{14}R_{15}$, in which each of $R_{10}$ to $R_{15}$ is independently hydrogen, $C_{1-6}$alkyl, aryl or aralkyl.

2. A compound selected from the group consisting of:

1-(pyrrolidin-1-yl)methyl-2-(3,4-dichlorophenyl)-acetyl-4,4-dimethyl-1,2,3,4-tetrahydroisoquinoline;

1-(pyrrolidin-1-yl)methyl-2-(4-trifluoromethylphenyl)acetyl-4,4-dimethyl-1,2,3,4-tetrahydroisoquinoline;

1-(pyrrolidin-1-yl)methyl-2-(5,6,7,8-tetrahydronaphth-2-yl)acetyl-4,4-dimethyl-1,2,3,4-tetrahydroisoquinoline;

1-(pyrrolidin-1-yl)methyl-2-(3,4-dichlorophenyl)-acetyl-3,3-dimethyl-1,2,3,4-tetrahydroisoquinoline;

(+)-1-(pyrrolidin-1-yl)methyl-2-(3,4-dichloro-phenyl)-acetyl-4,4-dimethyl-1,2,3,4-tetrahydroisoquino-quinoline; and (−)-1-(pyrrolidin-1-yl)methyl-2-(3,4-dichloro-phenyl)-acetyl-4,4-dimethyl-1,2,3,4-tetrahydroiso-quinoline;

3. A pharmaceutical composition comprising a compound according to claim 1, and a pharmaceutically acceptable carrier.

4. A pharmaceutical composition according to claim 3 in unit dosage form.

5. A method for the treatment of pain in mammals which comprises administering to the mammal in need of such treatment an effective amount of a compound of formula (I), as defined in claim 1, or a salt or solvate thereof.

* * * * *